United States Patent
Yang

(10) Patent No.: US 11,400,317 B2
(45) Date of Patent: *Aug. 2, 2022

(54) SYSTEMS AND METHODS FOR CALIBRATING AN ALIGNMENT DEVICE

(71) Applicant: SHANGHAI UNITED IMAGING HEALTHCARE CO., LTD., Shanghai (CN)

(72) Inventor: Hongcheng Yang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 766 days.

This patent is subject to a terminal disclaimer.

(21) Appl. No.: 15/686,035

(22) Filed: Aug. 24, 2017

(65) Prior Publication Data

US 2019/0054322 A1  Feb. 21, 2019

(30) Foreign Application Priority Data

Aug. 21, 2017 (CN) .......................... 2017 1 0718268

(51) Int. Cl.
*A61N 5/10* (2006.01)

(52) U.S. Cl.
CPC ......... *A61N 5/1081* (2013.01); *A61N 5/1075* (2013.01); *A61N 5/1084* (2013.01); *A61N 2005/1076* (2013.01)

(58) Field of Classification Search
CPC .......... A61N 2005/1076; A61N 5/1075; A61N 5/1081; A61N 5/1084
See application file for complete search history.

(56) References Cited

U.S. PATENT DOCUMENTS

| 4,296,329 A | 10/1981 | Mirabella |
| 6,670,618 B1 * | 12/2003 | Hartmann ............ A61N 5/1043 |
| | | 250/491.1 |

(Continued)

FOREIGN PATENT DOCUMENTS

| CN | 102049106 A | 5/2011 |
| CN | 202478416 U | 10/2012 |

(Continued)

OTHER PUBLICATIONS

Kai, Yang et al., A Geometric Calibration Method for Cone Beam CT Systems, Medical Physics Author manuscript, 2010, 40 pages.

(Continued)

*Primary Examiner* — Marcus H Taningco
(74) *Attorney, Agent, or Firm* — Metis IP LLC

(57) ABSTRACT

A method for calibrating an alignment device includes obtaining one or more projection images of a phantom having one or more surface indicators, the one or more surface indicators indicating a first coordinate system relating to the phantom, an origin of the first coordinate system overlapping with a calibration point of the phantom. The method further includes determining a difference between the first coordinate system and a second coordinate system based on the one or more projection images, the second coordinate system being relating to a medical system. The method further includes adjusting the phantom to an updated state according to the difference between the first coordinate system and the second coordinate system such that the first coordinate system overlaps with the second coordinate system. The method also includes adjusting an alignment device according to the one or more surface indicators in the updated state.

20 Claims, 10 Drawing Sheets

(56) References Cited

U.S. PATENT DOCUMENTS

| | | | | |
|---|---|---|---|---|
| 7,348,974 B2* | 3/2008 | Smith | ............... | A61N 5/1049 |
| | | | | 345/420 |
| 7,843,429 B2* | 11/2010 | Pryor | ............... | G06F 3/042 |
| | | | | 345/158 |
| 7,889,906 B2* | 2/2011 | Smith | ............... | A61N 5/1049 |
| | | | | 382/132 |
| 8,198,579 B2 | 6/2012 | Jeung | | |
| 8,441,476 B2* | 5/2013 | Gloudemans | ............... | G06K 9/346 |
| | | | | 345/419 |
| 11,110,301 B2* | 9/2021 | Yang | ............... | A61N 5/1081 |
| 2003/0002055 A1* | 1/2003 | Kilthau | ............... | B23K 26/02 |
| | | | | 356/614 |
| 2003/0058999 A1* | 3/2003 | Mitschke | ............... | A61B 6/583 |
| | | | | 378/207 |
| 2005/0094771 A1* | 5/2005 | Basu | ............... | A61B 6/032 |
| | | | | 378/207 |
| 2005/0117708 A1* | 6/2005 | Cho | ............... | A61B 6/547 |
| | | | | 378/164 |
| 2007/0076946 A1* | 4/2007 | Kunisaki | ............... | G01B 11/002 |
| | | | | 382/153 |
| 2007/0290125 A1* | 12/2007 | Wang | ............... | G01T 1/1648 |
| | | | | 250/252.1 |
| 2009/0052760 A1 | 2/2009 | Smith et al. | | |
| 2009/0187112 A1* | 7/2009 | Meir | ............... | A61B 5/113 |
| | | | | 600/534 |
| 2011/0116606 A1* | 5/2011 | Yankelevitz | ............... | A61B 5/1075 |
| | | | | 378/207 |
| 2013/0229495 A1* | 9/2013 | Bani-Hashemi | ............... | A61B 6/582 |
| | | | | 348/47 |
| 2015/0204989 A1 | 7/2015 | Ni et al. | | |
| 2015/0352376 A1 | 12/2015 | Wiggers et al. | | |
| 2016/0038029 A1* | 2/2016 | Darne | ............... | A61B 5/0071 |
| | | | | 600/427 |
| 2016/0129283 A1 | 5/2016 | Meir et al. | | |
| 2018/0014809 A1* | 1/2018 | Lin | ............... | A61B 6/583 |
| 2018/0339174 A1 | 11/2018 | Kilby et al. | | |

FOREIGN PATENT DOCUMENTS

| | | |
|---|---|---|
| CN | 203016973 U | 6/2013 |
| CN | 205831813 U | 12/2016 |
| CN | 106693215 A | 5/2017 |

OTHER PUBLICATIONS

J. Chetley Ford et al., Estimation of CT Cone-Beam Geometry Using a Novel Method insensitive to Phantom Fabrication Inaccuracy: implications for Isocenter Localization Accuracy, Medical Physics, 38(6): 2829-2840, 2011.

Mao, Weihua et al., Development of a QA Phantom and Automated Analysis Tool for Geometric Quality Assurance of on-Board MV and KV X-Ray imaging Systems, Medical Physics, 35(4): 1497-1506, 2008.

* cited by examiner

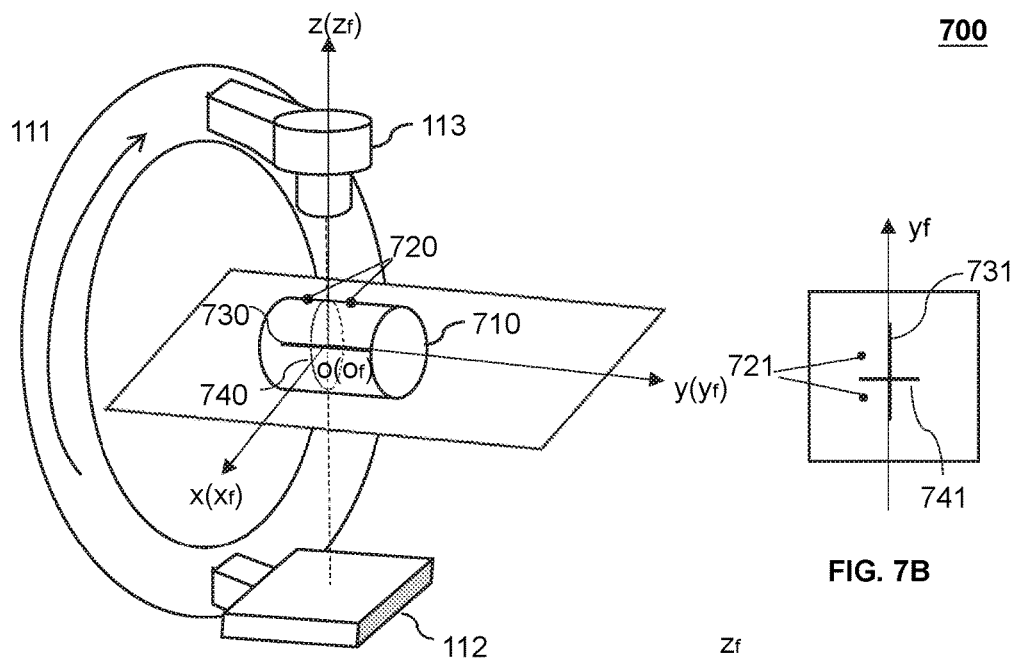
FIG. 7A
FIG. 7B
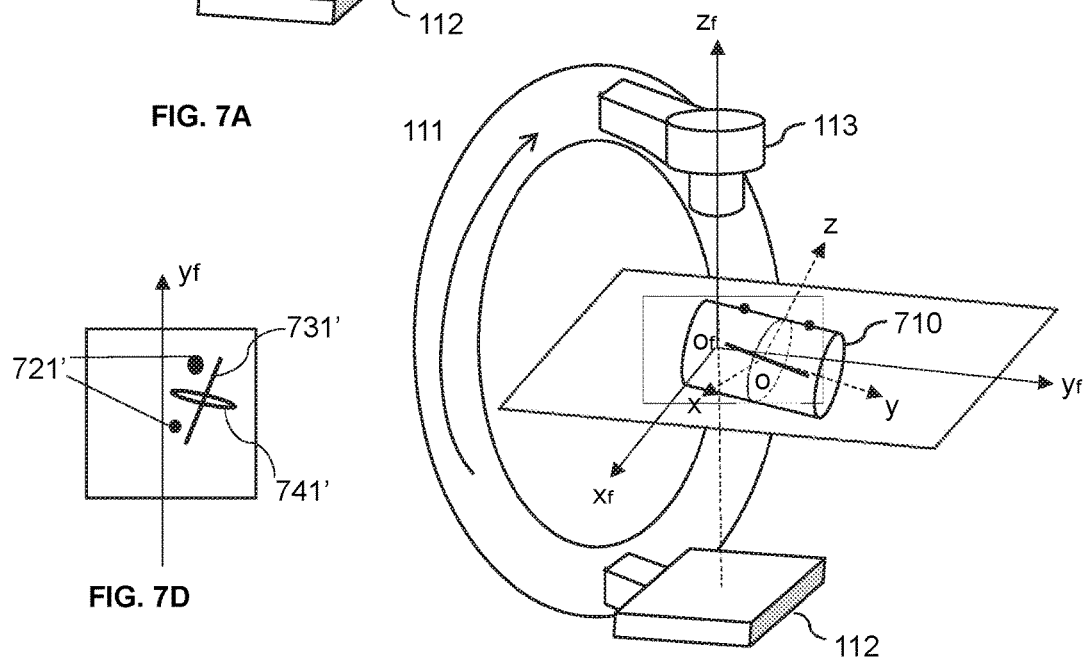
FIG. 7D
FIG. 7C
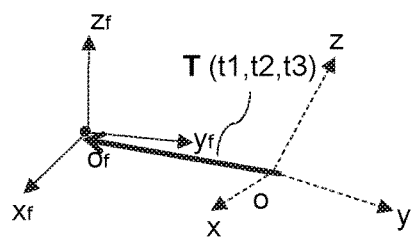
FIG. 7E
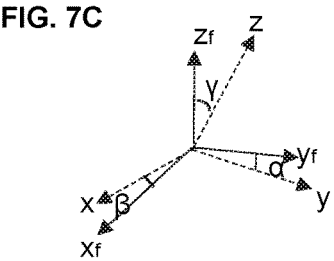
FIG. 7F

SYSTEMS AND METHODS FOR CALIBRATING AN ALIGNMENT DEVICE

CROSS-REFERENCE TO RELATED APPLICATIONS

This application claims priority of Chinese Application No. 201710718268.2 filed on Aug. 21, 2017, the entire contents of which are hereby incorporated by reference.

TECHNICAL FIELD

The present disclosure generally relates to systems and methods for calibrating an alignment device, and more particularly, to systems and methods for calibrating an alignment device using a phantom.

BACKGROUND

Radiotherapy technology becomes more and more important for treating tumors by directing a beam of ionizing radiation towards tumor tissue. In order to ensure the accuracy of delivering radiation to a target issue of a patient, the target issue of the patient should be positioned at the radiation isocenter of a medical system with the assistance of lasers. Generally, a set of lasers may be adjusted so that laser beams emitted by the set of lasers intersect at the radiation isocenter of the medical system. Thus, an accurate and efficient method for calibrating the laser beams is desirable.

SUMMARY

In one aspect of the present disclosure, a system is provided. The system may include at least one storage device storing a set of instructions. The system may further include at least one processor in communication with the at least one storage device, wherein when executing the set of instructions, the at least one processor may be configured to cause the system to: obtain one or more projection images of a phantom having one or more surface indicators, the one or more surface indicators indicating a first coordinate system relating to the phantom, an origin of the first coordinate system overlapping with a calibration point of the phantom. The at least one processor may also be configured to cause the system to determine a difference between the first coordinate system and a second coordinate system based on the one or more projection images, the second coordinate system being relating to a medical system. The at least one processor may further be configured to cause the system to adjust the phantom to an updated state according to the difference between the first coordinate system and the second coordinate system such that the first coordinate system overlaps with the second coordinate system. The at least one processor may also be configured to cause the system to adjust an alignment device according to the one or more surface indicators in the updated state.

In another aspect of the present disclosure, a method implemented on one system, including at least one processor and at least one storage is provided. The method may include obtaining one or more projection images of a phantom having one or more surface indicators, the one or more surface indicators indicating a first coordinate system relating to the phantom, an origin of the first coordinate system overlapping with a calibration point of the phantom. The method may also include determining a difference between the first coordinate system and a second coordinate system based on the one or more projection images, the second coordinate system being relating to a medical system. The method may further include adjusting the phantom to an updated state according to the difference between the first coordinate system and the second coordinate system such that the first coordinate system overlaps with the second coordinate system. The method may further include adjusting an alignment device according to the one or more surface indicators in the updated state.

In another aspect of the present disclosure, a non-transitory computer readable medium is provided. The non-transitory computer readable medium may include executable instructions that, wherein when executed by at least one processor, the executable instructions may cause the at least one processor to effectuate a method including obtaining one or more projection images of a phantom having one or more surface indicators, the one or more surface indicators indicating a first coordinate system relating to the phantom, an origin of the first coordinate system overlapping with a calibration point of the phantom; determining a difference between the first coordinate system and a second coordinate system based on the one or more projection images, the second coordinate system being relating to a medical system; adjusting the phantom to an updated state according to the difference between the first coordinate system and the second coordinate system such that the first coordinate system overlaps with the second coordinate system. The executable instructions may also cause the at least one processor to effectuate the method including adjusting an alignment device according to the one or more surface indicators in the updated state.

In some embodiments, the at least one processor may further be configured to cause the system to: before obtaining the one or more projection images, adjust the phantom to make the calibration point of the phantom roughly align with the radiation source of the medical system In some embodiments, the calibration point may include a center of the phantom or a point of the phantom away from the center of the phantom by a distance.

In some embodiments, the phantom may include at least one marker. To determine the difference between the first coordinate system and the second coordinate system based on one or more projection images of the phantom, the at least one processor may further be configured to cause the system to: determine at least one feature of the at least one marker in the one or more projection images, the feature including at least one of: a shape of the at least one marker, a size of the at least one maker, or a location of the at least one maker in the one or more projection images; and determine the difference between the first coordinate system and the second coordinate system based on the at least one feature of the at least one marker.

In some embodiments, the difference between the first coordinate system and the second coordinate system may include: a first difference indicating a displacement of an origin of the second coordinate system relative to the origin of the first coordinate system, or a second difference indicating one or more deflection angles of at least one axis of the second coordinate system relative to the corresponding axis of the first coordinate system.

In some embodiments, the system may instruct a movable support to adjust the phantom.

In some embodiments, the movable support may be an at least 4D movable support.

In some embodiments, the alignment device may include one or more lasers configured to emit a laser beam.

In some embodiments, the laser beam emitted by at least one of the one or more lasers may have two planes perpendicular to each other.

In some embodiments, the laser beam emitted by at least one of the one or more lasers may include one plane.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIGS. 7A and 7C illustrate exemplary scenarios in which a phantom is in different states according to some embodiments of the present disclosure;

FIGS. 7B and 7D show exemplary projection images according to some embodiments of the present disclosure;

FIGS. 7E and 7F show an exemplary difference between a first coordinate system and a second coordinate system according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by other expression if they achieve the same purpose.

Figure 2:
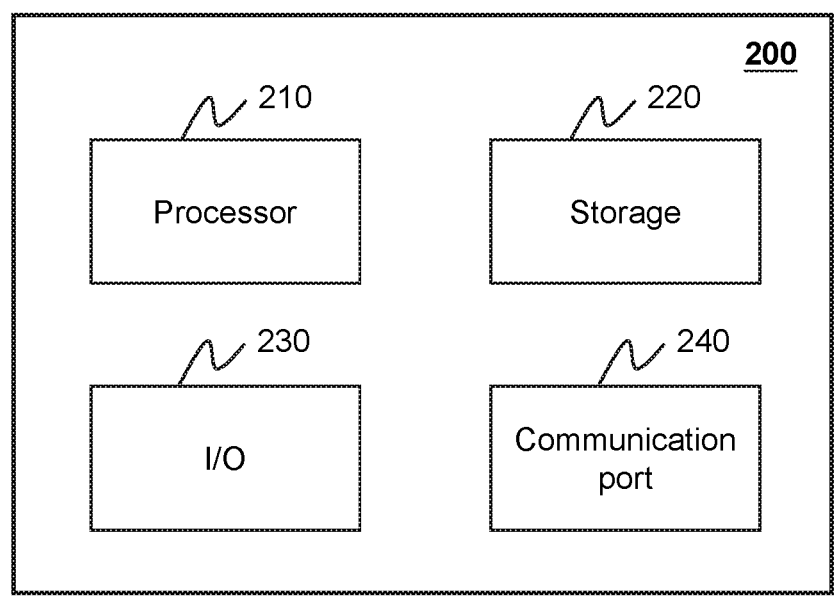
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., the processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to systems and methods for calibrating an alignment device used for a medical system. The alignment device may include one or more lasers configured to emit laser beams. In some embodiments, the alignment device may be calibrated according to a phantom. In some embodiments, a difference between a first coordinate system of the phantom and a second coordinate system of the medical machine may be determined using a geometric calibration method. Then the phantom may be adjusted to an updated state according to the difference between the first coordinate system and the second coordinate system such that the first coordinate system overlaps with the second coordinate system. The alignment device may be calibrated by aligning laser beams emitted by the one or more lasers with the corresponding surface indicators of the phantom in the updated state.

The term "radiation isocenter" refers to the radiation beam intersection of the gantry, collimator or couch rotation of a medical system with respect to a 3D reference coordinate system. For example, the radiation isocenter of the medical system may be a point at which radiation beams emitted from different gantry angles intersect.

The term "medical system" in the present disclosure may refer to a system in a medical field, including a computed tomography (CT) system, a cone-beam computed tomography (CBCT) system, a magnetic resonance imaging (MRI) system, a positron emission tomography (PET) system, a single photon emission computed tomography (SPECT) system, an ultrasonography system, a linear accelerator (LINAC), or the like, or any combination thereof.

In some embodiments, the phantom in the present disclosure may refer to an object used to calibrate the alignment device. The phantom may have a cylindrical, cubic, spherical shape, or be a phantom in a shape of scaffold, or a phantom with other forms. The phantom may include one or more markers (e.g., ball bearings, rods, rings) embedded on the phantom. The one or more markers may be used to determine a difference between a first coordinate system and a second coordinate system. The phantom may then be adjusted to an updated state according to the difference between the first coordinate system and the second coordinate system. Besides, the phantom may include one or more surface indicators. The number of the surface indicators may be any reasonable value. In some embodiments, the one or more surface indicators may be a cross. Particularly, one line of the cross may be parallel to a center axis of the phantom.

In some embodiments, the first coordinate system may be a coordinate system relating to the phantom. For example, the origin of the first coordinate system may overlap with the calibration point of the phantom. In some embodiments, the calibration point may include a center of the phantom, or a point of the phantom away from the center of the phantom by a known distance.

The first coordinate system may include three orthogonal axes. The three orthogonal axes may be called as a first axis, a second axis, and a third axis. The first axis (e.g., the y-axis shown in FIG. 7C) may be parallel to or overlap with a center axis of the phantom. The second axis (e.g., the z-axis shown in FIG. 7C) may overlap with a line connecting one of the one or more surface indicators and the calibration point of the phantom. The third axis (e.g., the x-axis shown in FIG. 7C) may be perpendicular to a plane determined by the first axis and the second axis.

In some embodiments, the second coordinate system may be a coordinate system relating to the medical system. For example, the origin of the second coordinate system may overlap with a radiation isocenter of the medical system. The second coordinate system may include three orthogonal axes. The three orthogonal axes may be called as a first axis, a second axis, and a third axis. The first axis (e.g., the $y_f$-axis shown in FIG. 7C) may overlap with a rotation axis of a gantry of the medical system. The second axis (e.g., the $z_f$-axis shown in FIG. 7C) and the third axis (e.g., the $x_f$-axis shown in FIG. 7C) may be in a rotation plane of the gantry of the medical system. The second axis may be parallel to or overlap with a line connecting the radiation source and the radiation isocenter when the gantry is at 0°. The third axis may be perpendicular to a plane determined by the first axis and the second axis.

For persons having ordinary skills in the art, a certain amount of variations, changes, and/or modifications may be deducted under the guidance of the present disclosure. Those variations, changes, and/or modifications do not depart from the scope of the present disclosure.

Figure 1A:
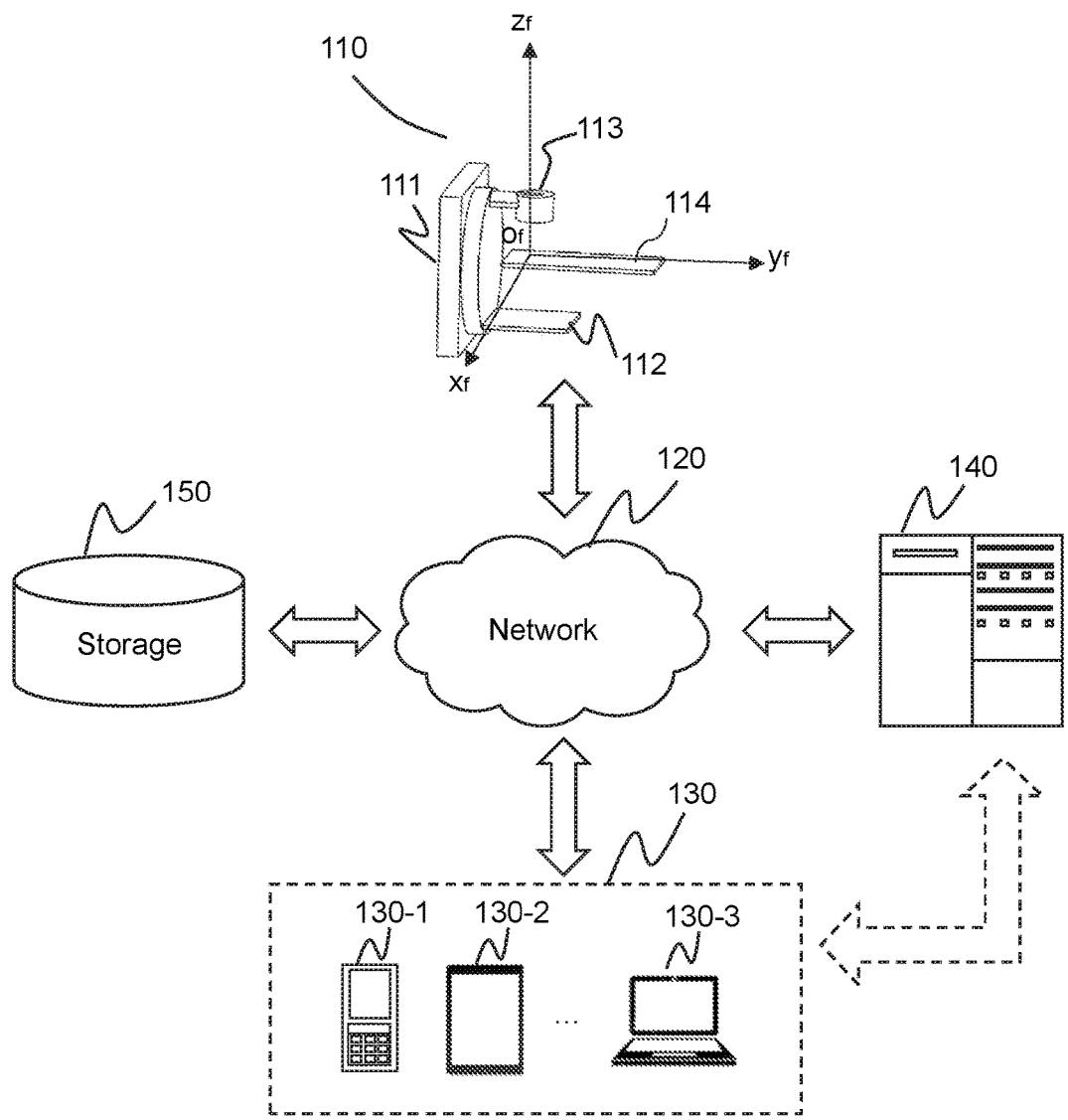
FIGS. 1A and 1B are schematic diagrams illustrating an exemplary medical system according to some embodiments of the present disclosure.
Figure 1B:
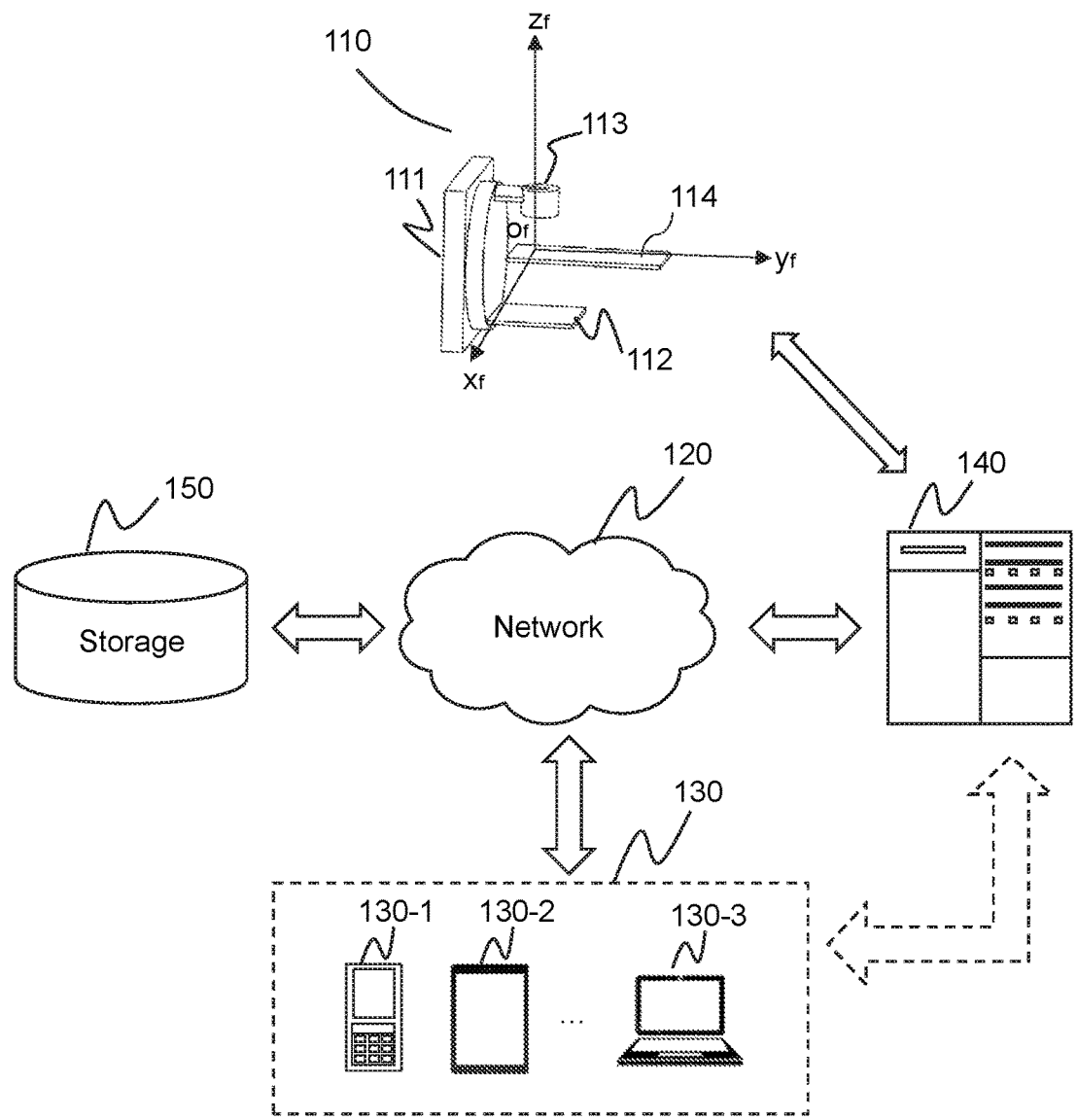

FIGS. 1A and 1B are schematic diagrams illustrating an exemplary medical system 100 according to some embodiments of the present disclosure. The medical system 100 may include a radiation device 110, a network 120, a terminal 130, a processing device 140, and a storage 150. The connection between the components in the medical system 100 may be variable. Merely by way of example, as illustrated in FIG. 1A, the radiation device 110 may be connected to the processing device 140 through the network 120. As another example, as illustrated in FIG. 1B, the radiation device 110 may be connected to the processing device 140 directly.

The radiation device 110 may include a gantry 111, a detector 112 (e.g., an electronic portal imaging device, EPID), a radiation source 113, and a subject table 114. The gantry 111 may support the detector 112, the radiation source 113. A subject to be scanned may be placed on the subject table 114. The radiation source 113 may emit radiation rays to the subject. In some embodiments, the radiation source 113 may emit rays with suitable energy (e.g., greater than 160 keV) for treatment. In some embodiments, the radiation source 113 may emit rays with suitable energy (e.g., generally less than 160 keV) for imaging. The detector 112 may detect radiation (e.g., X-ray) emitted from the radiation source 113. In some embodiments, the detector 112 may include a plurality of detector units. The detector units may include a scintillation detector (e.g., a detector consisting of GOS, cesium iodide) or a gas detector. The detector unit may be a flat panel detector. The detector unit may be a singlerow detector or a multi-rows detector. For the purposes of illustration, a Cartesian coordinate system is introduced based on a right-hand rule. As used herein, the Cartesian coordinate system may also be referred to as the second coordinate system relating to the medical system 100. The origin, $o_f$, of the second coordinate system may be an intersection of the rotation plane and the rotation axis, i.e., the radiation isocenter of the gantry 111. In some embodiments, the second coordinate system may be an International Electro-technical Commission (IEC) coordinate system. The IEC coordinate system may be a three-dimensional coordinate system. The IEC coordinate system may include a first axis ($y_f$-axis shown in FIGS. 1A and 1B), a second axis ($z_f$-axis shown in FIGS. 1A and 1B) perpendicular to the first axis, and a third axis ($x_f$-axis shown in FIGS. 1A and 1B) perpendicular to the first axis ($y_f$-axis) and the second axis ($z_f$-axis). As shown in FIG. 1A and/or 1B, the first axis ($y_f$-axis) overlaps with the rotation axis of the gantry 111. The third axis ($x_f$-axis) and the second axis ($z_f$-axis) are in the rotation plane of the gantry 111. The second axis ($z_f$-axis) is parallel to or overlap with a line connecting the radiation source 113 and the radiation isocenter when the gantry is at 0°. The third axis ($x_f$-axis) is perpendicular to a plane determined by the first axis ($y_f$-axis) and the second axis ($z_f$-axis).

The network 120 may facilitate exchange of information and/or data. In some embodiments, one or more components in the medical system 100 (e.g., the radiation device 110, the terminal 130, the processing device 140, or the storage 150) may send information and/or data to another component in the medical system 100 via the network 120. For example, the processing device 140 may obtain image data from the radiation device 110 via the network 120. As another example, the processing device 140 may obtain user instructions from the terminal 130 via the network 120. In some embodiments, the network 120 may be any type of wired or wireless network, or combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof. In some embodiments, the network 120 may include one or more network access points. For example, the network 120 may include wired or wireless network access points such as base stations and/or internet exchange points through which one or more components of the medical system 100 may be connected to the network 120 to exchange data and/or information.

The terminal 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, a smart footgear, smart glass, a smart helmet, a smart watch, smart clothing, a smart backpack, a smart accessory, or the like, or any combination thereof. In some embodiments, the smart mobile device may include a smartphone, a personal digital assistance (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. In some embodiments, the terminal 130 may be part of the processing device 140. In some embodiments, the terminal 130 may be omitted.

The processing device 140 may process data and/or information obtained from the radiation device 110, the terminal 130, or the storage 150. For example, the processing device 140 may process image data and determine a regularization item that may be used to modify the image data. In some embodiments, the processing device 140 may be a single server or a server group. The server group may be centralized or distributed. In some embodiments, the processing device 140 may be local or remote. For example, the processing device 140 may access information and/or data stored in the radiation device 110, the terminal 130, and/or the storage 150 via the network 120. As another example, the processing device 140 may be directly connected to the radiation device 110, the terminal 130 and/or the storage 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage 150 may store data and/or instructions. In some embodiments, the storage 150 may store data obtained from the terminal 130 and/or the processing device 140. In some embodiments, the storage 150 may store data and/or instructions that the processing device 140 may execute or use to perform exemplary methods described in the present disclosure. In some embodiments, the storage 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more components in the medical system 100 (e.g., the processing device 140, the terminal 130). One or more components of the medical system 100 may access the data or instructions stored in the storage 150 via the network 120. In some embodiments, the storage 150 may be directly connected to or communicate with one or more components in the medical system 100 (e.g., the processing device 140, the terminal 130). In some embodiments, the storage 150 may be part of the processing device 140.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 140 in accordance with techniques described herein. The computer instructions may include routines, programs, objects, components, data structures, procedures, modules, and functions, which perform particular functions described herein. For example, the processor 210 may process image data obtained from the radiation device 110, the terminal 130, the storage 150, or any other component of the medical system 100. In some embodiments, the processor 210 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC system (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two different processors jointly or separately in the computing device 200 (e.g., a first processor executes step A and a second processor executes step B, or the first and second processors jointly execute steps A and B).

The storage 220 may store data/information obtained from the radiation device 110, the terminal 130, the storage 150, or any other component of the medical system 100. In some embodiments, the storage 220 may include a mass storage, removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for determining a regularization item.

The I/O 230 may input or output signals, data, or information. In some embodiments, the I/O 230 may enable a user interaction with the processing device 140. In some embodiments, the I/O 230 may include an input device and an output device. Exemplary input device may include a keyboard, a mouse, a touch screen, a microphone, or the like, or a combination thereof. Exemplary output device may include a display device, a loudspeaker, a printer, a projector, or the like, or a combination thereof. Exemplary display device may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the radiation device 110, the terminal 130, or the storage 150. The connection may be a wired connection, a wireless connection, or combination of both that enables data transmission and reception. The wired connection may include an electrical cable, optical cable, telephone wire, or the like, or any combination thereof. The wireless connection may include Bluetooth, Wi-Fi, WiMax, WLAN, ZigBee, mobile network (e.g., 3G, 4G, 5G), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
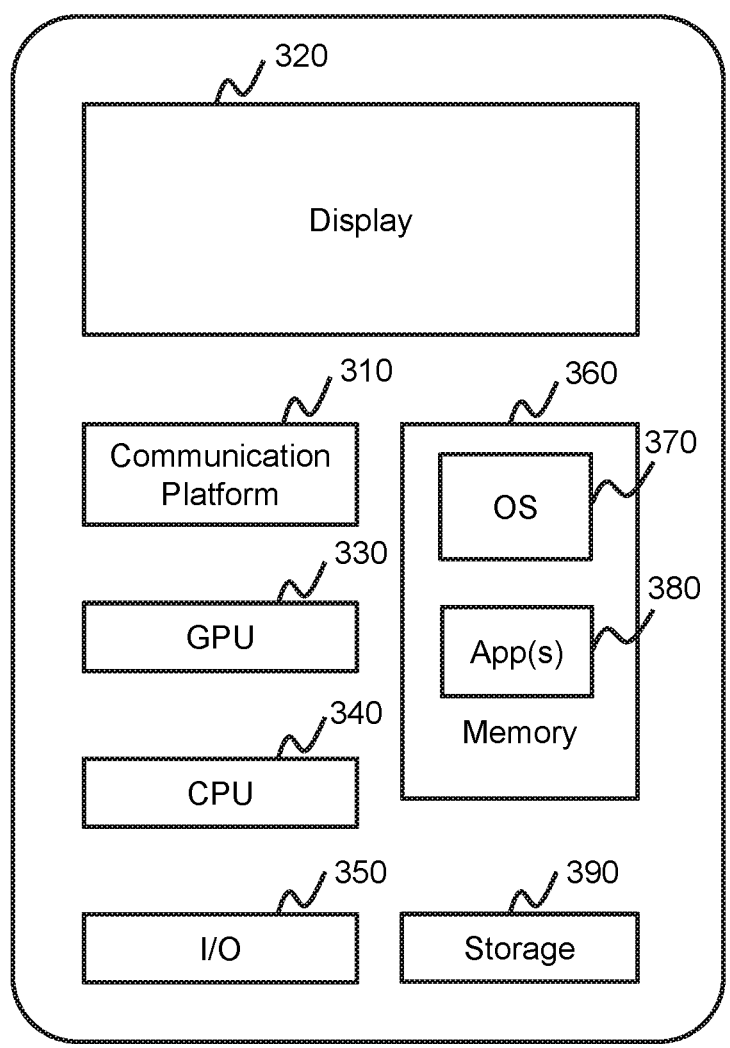
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the medical system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to calibrating the alignment device as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
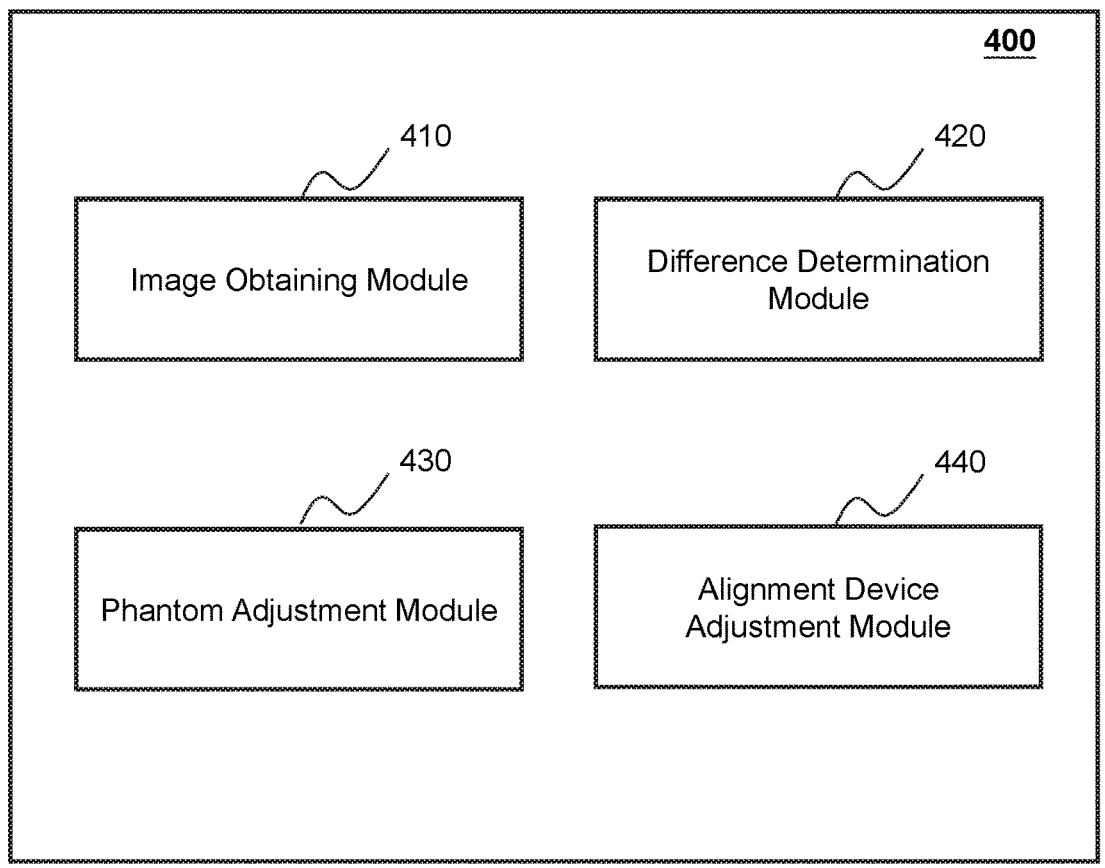
FIG. 4 is a schematic diagram illustrating an exemplary processor according to some embodiments of the present disclosure.

FIG. 4 is a schematic diagram illustrating an exemplary processor 400 according to some embodiments of the present disclosure. The processor 400 may be implemented on the computing device 200 (e.g., the processor 210) illustrated in FIG. 2. The processor 400 may include an image obtaining module 410, a difference determination module 420, a phantom adjustment module 430, and an alignment device adjustment module 440.

The image obtaining module 410 may be configured to obtain one or more projection images of a phantom. In some embodiments, the phantom may have a cylindrical, cubic, spherical shape, or be a phantom in a shape of scaffold. The phantom may include one or more surface indicators. The one or more surface indicators may indicate a first coordinate system relating to the phantom. The first coordinate system may be described in detail in connection with FIG. 5. The origin of the first coordinate system may overlap with a calibration point of the phantom. Specifically, the calibration point may be a point at which extended lines relating to the one or more surface indicators intersect in the phantom (e.g., a calibration point o 830 in FIGS. 8A and 8B). In some embodiments, the calibration point of the phantom may include a center of the phantom or a point of the phantom away from the center of the phantom by a known distance. In some embodiments, the one or more surface indicators may have a cross shape.

The difference determination module 420 may be configured to determine a difference between the first coordinate system and the second coordinate system based on the one or more projection images. In some embodiments, the difference between the first coordinate system and the second coordinate system may include a first difference indicating a displacement of the origin of the second coordinate system relative to the origin of the first coordinate system (i.e., a displacement of the radiation isocenter of the medical system relative to the calibration point of the phantom). The difference between the first coordinate system and the second coordinate system may also include a second difference indicating one or more deflection angles of at least one axis of the second coordinate system relative to the corresponding axis of the first coordinate system. In some embodiments, the difference determination module 420 may determine the difference between the first coordinate system and the second coordinate system using a geometric calibration method. Specifically, the difference determination module 420 may determine one or more features of the one or more markers in the one or more projection images. The difference determination module 420 may determine the difference between the first coordinate system and the second coordinate system based on the one or more features of the one or more markers in the one or more projection images.

The phantom adjustment module 430 may be configured to adjust the phantom to an updated state such that the first coordinate system overlaps with the second coordinate system. In some embodiments, the phantom adjustment module 430 may adjust the phantom to the updated state according to the difference between the first coordinate system and the second coordinate system. In some embodiments, the phantom adjustment module 430 may first adjust the phantom according to the first difference and then adjust the phantom to the updated state according to the second difference. Alternatively, the phantom adjustment module 430 may first adjust the phantom according to the second difference, and then adjust the phantom to the updated state according to the first difference.

The alignment device adjustment module 440 may be configured to adjust an alignment device according to the one or more surface indicators of the phantom in the updated state. The alignment device may include one or more lasers. The one or more lasers may emit laser beams. In some embodiments, each of the one or more lasers may correspond to one of the one or more surface indicators of the phantom. The alignment device adjustment module 440 may adjust the one or more lasers to make the laser beams align with the corresponding surface indicators of the phantom. Thus, the laser beams emitted by the alignment device may intersect at the radiation isocenter of the medical system.

It should be noted that the above description of the processor 400 is provided for the purpose of illustration, and is not intended to limit the scope of the present disclosure. For persons having ordinary skills in the art, multiple variations and modifications may be made under the teaching of the present disclosure. However, those variations and modifications do not depart from the scope of the present disclosure. For example, the difference determination module 420 and the phantom adjustment module 430 may be integrated into one module, configured to determine the difference between the first coordinate system and the second coordinate system and adjust the phantom to the updated state. As another example, some of the modules may be installed in a different device separated from the other modules. Merely by way of example, the alignment device adjustment module 440 may reside in a device, and other modules may reside on a different device.

Figure 5:
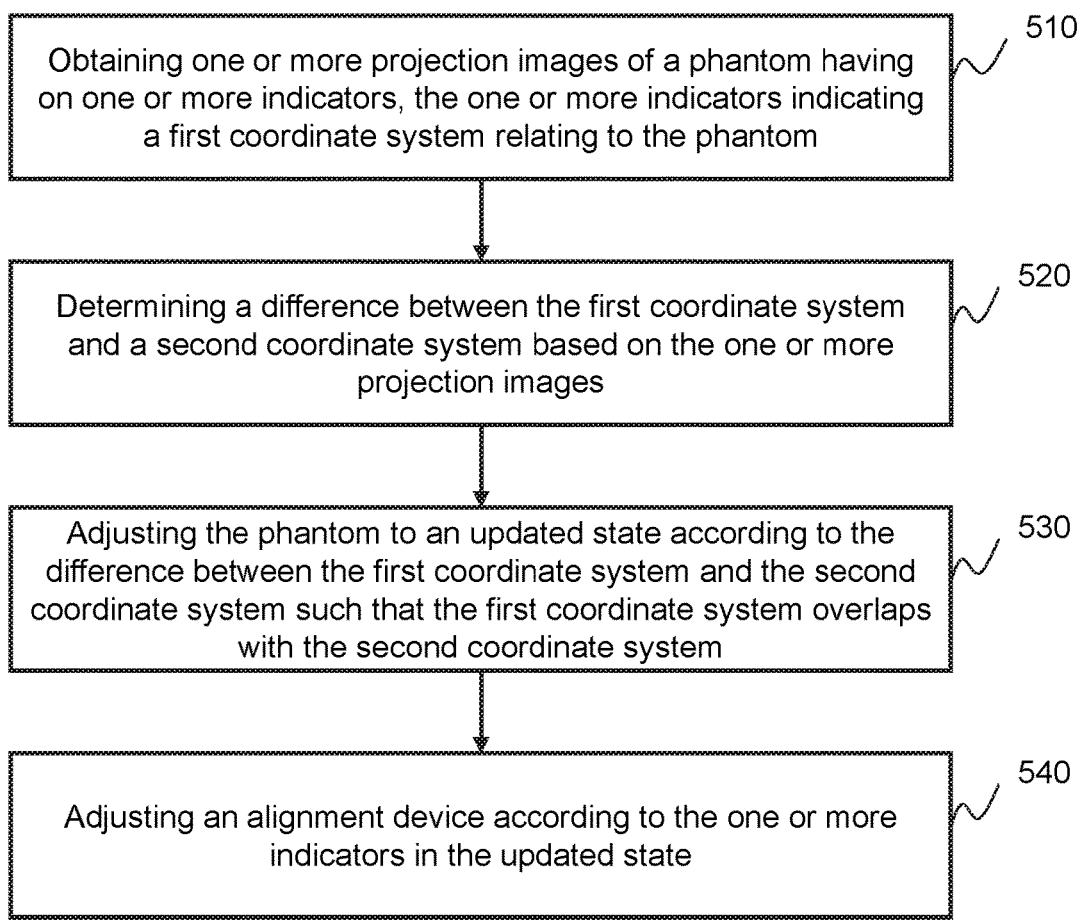
FIG. 5 is a flowchart illustrating an exemplary process for calibrating an alignment device according to some embodiments of the present disclosure.

FIG. 5 is a flowchart illustrating an exemplary process 500 for calibrating an alignment device according to some embodiments of the present disclosure. The process 500 may be executed by the medical system 100. For example, the process 500 may be implemented as a set of instructions (e.g., an application) stored in the storage 220. The processor 210 may execute the set of instructions and may accordingly be directed to perform the process 500. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 5 and described herein is not intended to be limiting.

In 510, the image obtaining module 410 may obtain one or more projection images of a phantom having one or more surface indicators. The one or more surface indicators may indicate a first coordinate system relating to the phantom. In some embodiments, the phantom may have a cylindrical, cubic, spherical shape, or be a phantom in other shape. The origin of the first coordinate system may overlap with a calibration point of the phantom. The calibration point may be a point at which extended lines relating to the one or more surface indicators intersect in the phantom (e.g., a calibration point o 830 in FIGS. 8A and 8B). In some embodiments, the calibration point of the phantom may be the center of the phantom. Alternatively or additionally, the calibration point of the phantom may include a point of the phantom away from the center of the phantom by a known distance.

In some embodiments, the first coordinate system may include three orthogonal axes. The first axis may be parallel to or overlap with the center axis of the phantom (e.g., the y-axis in FIG. 8A). The center axis of the phantom herein refers to a line through the center of the phantom, which may be used to represent the orientation of the phantom. The phantom may be in any suitable shape. For example, for a cylindrical phantom, the center axis of the cylindrical phantom may be a line connecting the center of the top surface and the center of the bottom surface of the cylindrical phantom. For a cubic phantom, the center axis of the cubic phantom may be a line connecting the center of any two opposite surfaces of the cubic phantom. For example, if the calibration point lies in the center of the phantom, the first axis may overlap with the center axis of the phantom. Alternatively, if the calibration point lies on the point of the phantom away from the center of the phantom by a known distance, the first axis may be parallel to the center axis of the phantom. The second axis may overlap with a line connecting one of the one or more surface indicators and the calibration point (e.g., the z-axis in FIG. 8A). The third axis may be perpendicular to a plane determined by the first axis and the second axis (e.g., the x-axis in FIG. 8A).

In some embodiments, the one or more surface indicators may have a cross shape. In some embodiments, the one or more surface indicators may have other shapes. The locations of the one or more surface indicators on the phantom may be determined according to specific conditions. For example, for a cylindrical phantom, the one or more surface indicators may be on the side wall of the cylindrical phantom, or the top or bottom surface of the cylindrical phantom. The number of the one or more surface indicators may be any suitable number, e.g., two, three, four, five.

In some embodiments, the phantom may include one or more markers (e.g., ball bearings, rods, rings) on the surface of or embedded in the phantom. The locations of the one or more markers of the phantom may be determined by the coordinates of the one or more markers in the first coordinate system.

In 520, the difference determination module 420 may determine a difference between the first coordinate system and the second coordinate system based on the one or more projection images. The second coordinate system may relate to the medical system. The origin, $o_f$, of the second coordinate system may be an intersection of the rotation planed and the rotation axis, i.e., the radiation isocenter of medical system. The radiation isocenter of the medical system may be determined based on the difference between the first coordinate system and the second coordinate system and the origin of the first coordinate system of the phantom. The second coordinate system of the medical system may be determined accordingly. The first axis ($y_f$-axis) of the second coordinate system may overlap with the rotation axis of the gantry 111. The second axis ($z_f$-axis) of the second coordinate system and the third axis ($x_f$-axis) of the second coordinate system may be in the rotation plane of the gantry 111. The second axis ($z_f$-axis) of the second coordinate system may be parallel to or overlap with a line connecting the radiation source 113 and the radiation isocenter when the gantry 111 is at 0°. The third axis ($x_f$-axis) of the second coordinate system may be perpendicular to the first axis ($y_f$-axis) and the second axis ($z_f$-axis).

The difference between the first coordinate system and the second coordinate system may include a first difference indicating a displacement of the origin of the second coordinate system relative to the origin of the first coordinate system (i.e., a displacement of the radiation isocenter of the medical system relative to the calibration point of the phantom). In some embodiments, the difference between the first coordinate system and the second coordinate system may also include a second difference indicating one or more deflection angles of at least one axis of the second coordinate system relative to the corresponding axis of the first coordinate system.

Figure 6A:
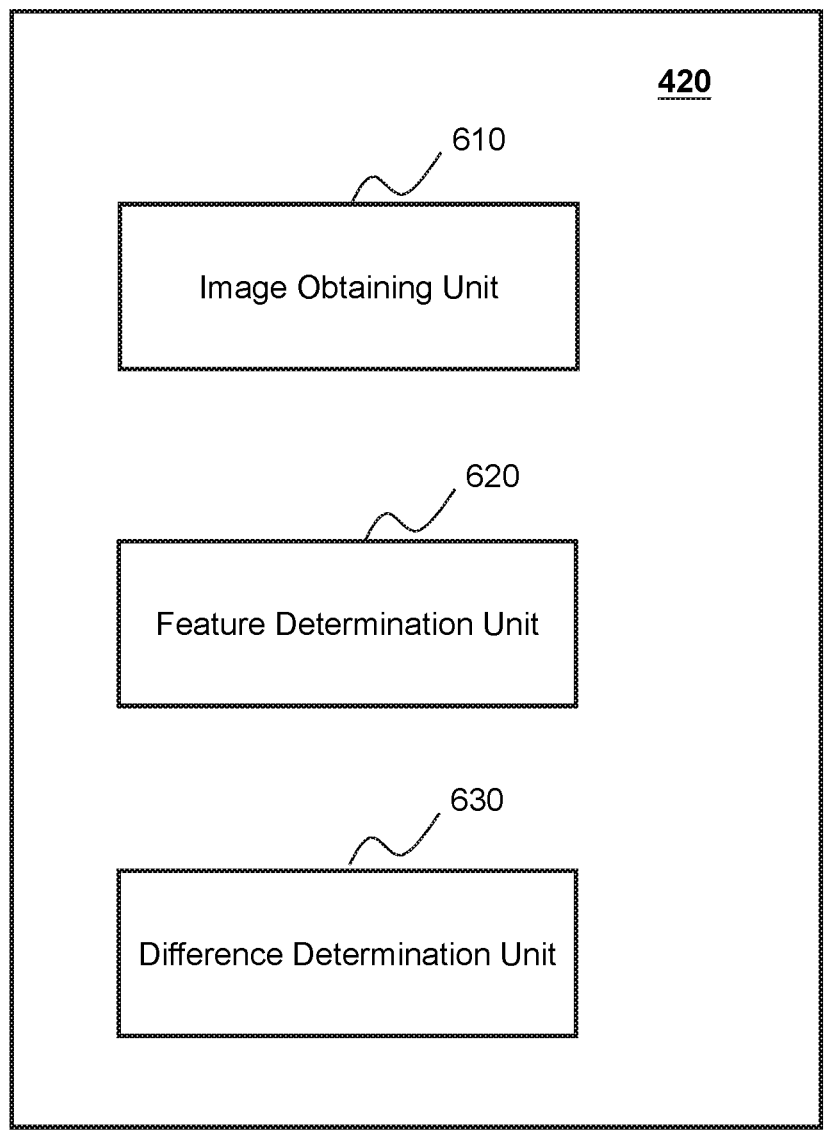
FIG. 6A is a schematic diagram illustrating an exemplary difference determination module according to some embodiments of the present disclosure.
Figure 6B:
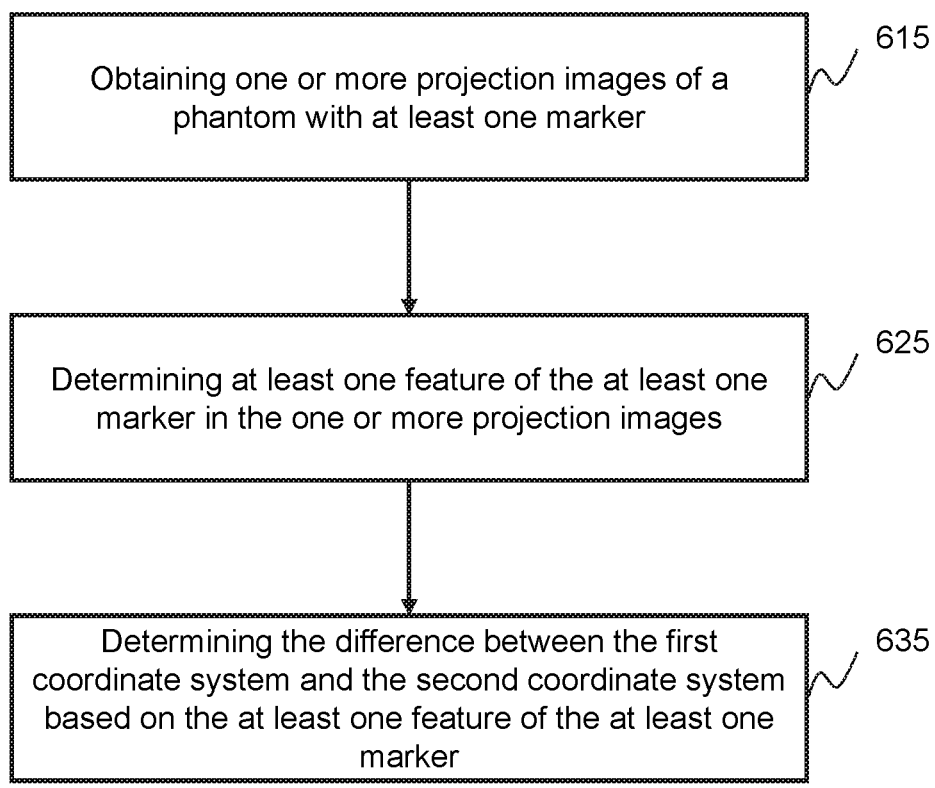
FIG. 6B is a flowchart illustrating an exemplary process for determining a difference between a first coordinate system and a second coordinate system according to some embodiments of the present disclosure.

In some embodiments, the difference between the first coordinate system and the second coordinate system based on the one or more projection images may be determined according to an exemplary process 600 illustrated in FIG. 6B.

In 530, the phantom adjustment module 430 may adjust the phantom to an updated state according to the difference between the first coordinate system and the second coordinate system such that the first coordinate system overlaps with the second coordinate system. The phantom adjustment module 430 may adjust the phantom to the updated state according to the determined difference by adjusting a movable support. In some embodiments, the movable support may be the subject table 114. In some embodiments, the movable support may be a device placed on the subject table 114. The movable support may include a multi-dimensional movable support. For example, the movable support may be a 3D movable support that may be movable along three directions in the space (e.g., a direction parallel to the $x_f$-axis, a direction parallel to the $y_f$-axis, a direction parallel to the $z_f$-axis). As another example, the movable support may be a 4D movable support that may be movable along three directions in the space and be rotatable around one direction parallel to or coinciding with the $x_f$-axis, the $y_f$-axis, or the $z_f$-axis. Particularly, the 4D movable support may be rotatable around the direction parallel to or coinciding with the $z_f$-axis. As yet another example, the movable support may be a 6D movable support that may be movable along three directions in the space and be rotatable around any direction parallel to or coinciding with the the $x_f$-axis, the $y_f$-axis, or the $z_f$-axis. In some embodiments, the phantom adjustment module 430 may first adjust the phantom according to the first difference and then adjust the phantom to the updated state according to the second difference. Alternatively, the phantom adjustment module 430 may first adjust the phantom according to the second difference and then adjust the phantom to the updated state according to the first difference.

Figure 9A:
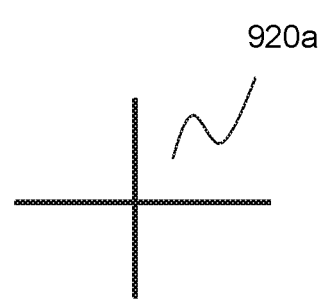
FIGS. 9A and 9B show projections of exemplary laser beams according to some embodiments of the present disclosure.
Figure 9B:
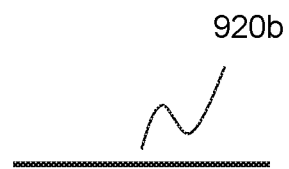

In 540, the alignment device adjustment module 440 may adjust an alignment device according to the one or more surface indicators of the phantom in the updated state. In some embodiments, the alignment device may include one or more lasers. The one or more lasers may emit laser beams. In some embodiments, the laser beam may include two planes perpendicular to each other, and the projection of the laser beam may be a cross (e.g., a cross 920a shown in FIG. 9A). In some embodiments, the laser beam may only include one plane, and the projection of the laser beam may be a line (e.g., a line 920b shown in FIG. 9B). Each of the one or more lasers may correspond to one of the one or more surface indicators of the phantom. The alignment device adjustment module 440 may adjust the one or more lasers to make the laser beams align with the corresponding surface indicator(s) of the phantom in the updated state. In some embodiments, the one or more lasers may be mounted on one or more movable supports. The alignment device adjustment module 440 may align the laser beams emitted by the one or more lasers with the corresponding surface indicator(s) by adjusting the movable supports. Thus, the laser beams emitted by the alignment device may intersect at the radiation isocenter of the medical system. In some embodiments, the one or more lasers may be mounted on a wall, the subject table 114, or any other device. In some embodiments, a user may manually adjust the one or more lasers to align the laser beams emitted by the one or more lasers with the corresponding surface indicator(s) of the phantom in the updated state.

Figure 8A:
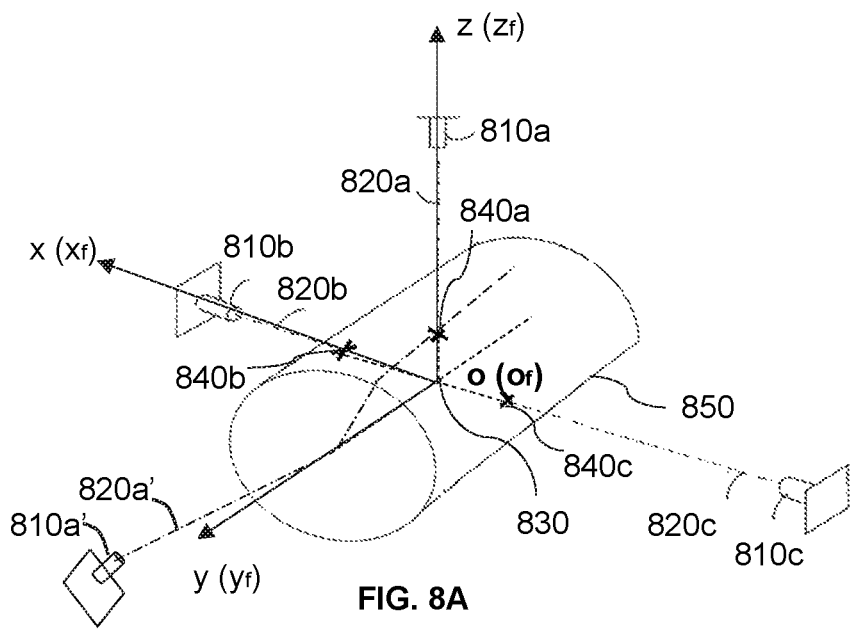
FIGS. 8A and 8B are schematic diagrams illustrating the alignment of lasers with corresponding surface indicators according to some embodiments of the present disclosure.
Figure 8B:
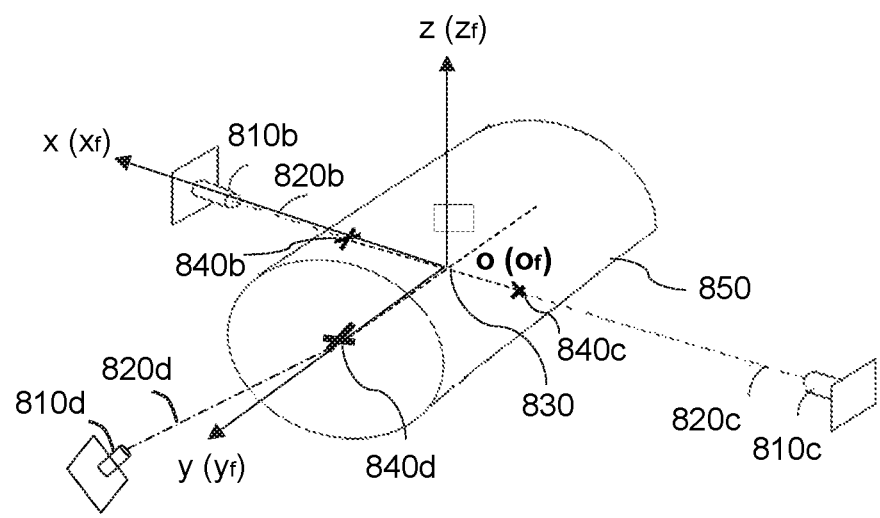

For the purposes of illustration, FIGS. 8A and 8B are schematic diagrams illustrating the alignment of one or more lasers of an alignment device with the corresponding surface indicators of the phantom. In FIGS. 8A and 8B, a phantom 850 is an exemplary cylinder phantom, and the alignment device includes three lasers 810a, 810b, and 810c. It should be understood that it is merely an example, and not intended to be limiting. The phantom 850 has been adjusted to the updated state under which the first coordinate system of the phantom overlaps with the second coordinate system of the medical system.

As shown in FIG. 8A, the one or more surface indicators (e.g., 840a, 840b, and 840c) are on the side wall of the phantom 850. The first coordinate system of the phantom overlaps with the second coordinate system of the medical system. In the updated state, a line connecting the first surface indicator 840a and the calibration point o 830 (the z-axis of the first coordinate system) overlaps with the $z_f$-axis of the second coordinate system, and a line connecting the second surface indicator 840b (or the third surface indicator 840c) and the calibration point o 830 (the x-axis of the first coordinate system) overlaps with the $x_f$-axis of the second coordinate system. The alignment device adjustment module 440 may adjust the alignment device based on the surface indicators in the updated state.

In FIG. 8A, the alignment device may include three lasers, e.g., a first laser 810a, a second laser 810b, a third laser 810c. The first laser 810a may correspond to the first surface indicator 840a. The second laser 810b may correspond to the second surface indicator 840b. The third laser 810c may correspond to the third indictor 840c. In some embodiment, the first laser 810a may be mounted on the roof of a space holding the subject table 114, and the second laser 810b and the third laser 810c may be mounted two opposite walls of the space, respectively.

The first laser 810a may emit a first laser beam 820a. The second laser 810b may emit a second laser beam 820b. The third laser 810c may emit a third laser beam 820c. In some embodiments, the laser beam (e.g., 820a, 820b, or 820c) may include two planes perpendicular to each other, i.e., the projection of the laser beam is a cross (e.g., the cross 920a in FIG. 9A). In some embodiments, the laser beam (e.g., 820a, 820b, or 820c) may include one plane, i.e., the projection of the laser beam is a line (e.g., the line 920b in FIG. 9B).

The alignment device adjustment module 440 may adjust the lasers to make the laser beams align with the corresponding surface indicators of the phantom. The lasers may be adjusted simultaneously, or in sequence. The alignment device adjustment module 440 may adjust the second laser 810b to make the second laser beam 820b align with the second surface indicator 840b. The projection of the second laser beam 820b may overlap with the cross of the second surface indicator 840b.

The alignment device adjustment module 440 may adjust the third laser 810c using the same method. As the line connecting the second surface indicator 840b and the third surface indicator 840c overlaps with the $x_f$-axis of the second coordinate system of the medical system, a line connecting the second laser 810b and the third laser 810c may overlap with the $x_f$-axis of the second coordinate system of the medical system and be parallel to the horizontal plane and perpendicular to the rotation axis of the gantry 111.

The alignment device adjustment module 440 may adjust the first laser 810a to make the first laser beam 820a align with the first surface indicator 840a. In some embodiments, the projection of the first laser beam 820a may overlap with the cross of the first surface indicator 840a. A line connecting the first laser 810a and the calibration point o 830 may overlap with the $z_f$-axis of the second coordinate system. In some embodiments, the projection of the first laser beam 820a may overlap with one line of the cross of the first surface indicator 840a. The line of the cross of the first surface indicator 840a may be parallel to the y-axis of the first coordinate system of the phantom 850.

In some embodiments, the first laser beam 820a may include two planes perpendicular to each other. Alternatively or additionally, the first laser beam 820a may include one plane, and the projection of the plane is parallel to or overlaps with the y-axis of the first coordinate system of the phantom 850. Thus, the position of the first laser 810a may be flexible, as long as the projection of the first laser beam 820a overlaps with one line of the first surface indicator 840a. For example, the first laser 810a may be adjusted so that the projection of the first laser beam 820a is parallel to or overlaps with the y-axis of the first coordinate system of the phantom 850. For example, the first laser 810a may be changed to a location corresponding to an end of the subject table 114 (e.g., a wall facing the end of the subject table 114). The end of the subject table 114 may refer to the end far from the gantry 111, or near the gantry 111. The changed first laser 810a is represented by 810a', and a laser beam emitted by 810a' is represented by 820a'. One plane of the laser beam 820a' may be projected on the top or bottom surface of the phantom 850 and the side wall of the phantom 850 (as shown in FIG. 8A). The alignment device adjustment module 440 may adjust the laser 810a' to make the projection of the plane of the laser beam 820' on the side wall of the phantom 850 overlap with one line of the first surface indicator 840a (e.g., a line parallel to the y-axis of the first coordinate system of the phantom 850). Thus, the three laser beams (820a (or 820a'), 820b, and 820c) intersect at the calibration point o 830.

FIG. 8B shows another exemplary phantom. As shown in FIG. 8B, the first surface indicator (labeled as 840d) is on a top surface or a bottom surface of the phantom 850, and the second surface indicator 840b and the third surface indicator 840c are on the side wall of the phantom 850. The first coordinate system of the phantom overlaps with the second coordinate system of the medical system. In the updated state, a line connecting the first surface indicator 840d and the calibration point o 830 (the y-axis of the first coordinate system) overlaps with the $y_f$-axis of the second coordinate system of the medical system (the rotation axis of the gantry 111 of the medical system), a line connecting the second surface indicator 840b (or the third surface indicator 840c) and the calibration point o 830 (the x-axis of the first coordinate system) overlaps with $x_f$-axis of the second coordinate system. The alignment device adjustment module 440 may adjust the alignment device based on the surface indicators.

In FIG. 8B, the alignment device may include three lasers, e.g., a first laser 810d, a second laser 810b, a third laser 810c, corresponding to the three surface indicators. The first laser 810d may correspond to the first surface indicator 840d. The second laser 810b may correspond to the second surface indicator 840b. The third laser 810c may correspond to the third surface indicator 840c. In some embodiments, the first laser 810d may be mounted on a wall facing the end of the subject table 114, and the second laser 810b and the third laser 810c may be mounted two opposite walls of the space, respectively.

The first laser 810d may emit a first laser beam 820d. The second laser 810b may emit a second laser beam 820b. The third laser 810c may emit a third laser beam 820c. The alignment device adjustment module 440 may adjust the lasers to make the laser beams align with the corresponding surface indicators of the phantom. The lasers may be adjusted simultaneously or in sequence. The adjustment of the second laser 810b and the third laser 810c is same with that in connection with FIG. 8A. Then a line connecting the second laser 810b and the third laser 810c may overlap with the $x_f$-axis of the second coordinate system of the medical system and be parallel to the horizontal plane and perpendicular to the rotation axis of the gantry 111.

The alignment device adjustment module 440 may adjust the first laser 810d to make the first laser beam 820d align with the first surface indicator 840d. In some embodiments, the projection of the first laser beam 820d may overlap with the cross of the first surface indicator 840d. A line connecting the first laser 810d and the calibration point o 830 may overlap with the y-axis of the first coordinate system of the phantom 850. In some embodiments, the projection of the first laser beam 820d may overlap with one line of the cross of the first surface indicator 840d.

The first laser beam 820d may include two planes perpendicular to each other. Alternatively or additionally, the first laser beam 820d may include one plane, and the projection of the plane on the top or bottom surface of the phantom 850 is parallel to the z-axis of the first coordinate system. The position of the first laser 810d may be flexible, as long as the projection of the plane on the top or bottom surface of the phantom 850 is parallel to the z-axis of the first coordinate system. Finally, the three laser beams (820d, 820b, and 820c) may intersect at the calibration point o 830.

It should be noted that the above description of the process 500 for calibrating the alignment device is provided for the purpose of illustration, and is not intended to limit the scope of the present disclosure. For persons having ordinary skills in the art, multiple variations and modifications may be made under the teaching of the present disclosure. However, those variations and modifications do not depart from the scope of the present disclosure. In some embodiments, the process 500 may also include other steps. For example, before obtaining the one or more projection images, the process 500 may include adjusting the phantom to make the calibration point of the phantom roughly overlap with the radiation isocenter of the medical system. In some embodiment, the medical system (e.g., the radiation source) may include a crosshair. Before obtaining one or more projection images, the phantom may be adjusted through the movable support so that the projection of the crosshair of the medical system may overlap with one of the one or more surface indicators when the phantom is placed on the subject table 114. Thus, the radiation source may align with the calibration point of the phantom roughly, and the intersection of the laser beam emitted by the lasers in the system may overlap with the radiation isocenter of the medical system roughly.

FIG. 6A is a schematic diagram illustrating an exemplary difference determination module 420 according to some embodiments of the present disclosure. The difference determination module 420 may be implemented on the computing device 200 (e.g., the processor 210) illustrated in FIG. 2. In some embodiments, the difference determination module 420 may include an image obtaining unit 610, a feature determination unit 620, and a difference determination unit 630.

The image obtaining unit 610 may be configured to obtain one or more projection images of a phantom with at least one marker. In some embodiments, the image obtaining unit 610 may obtain the one or more projection images of the phantom from the image obtaining module 410 and/or the storage 220. In some embodiments, the attenuation coefficient of the one or more markers on the phantom may be different from that of the phantom. For example, the attenuation coefficient of the one or more markers may be larger or less than that of the phantom. Besides, the attenuation coefficient of the one or more markers on the phantom may be the same or different.

The feature determination unit 620 may be configured to determine at least one feature of the at least one marker in the one or more projection images at one or more gantry angles. The at least one feature of the at least one marker may include a shape of the at least one marker, a size of the at least one marker, or a location of the at least one marker in the one or more projection images. In some embodiments, the feature may include relative locations between any two of the one or more markers in the one or more projection images.

The difference determination unit 630 may be configured to determine the difference between the first coordinate system and the second coordinate system based on the at least one feature of the at least one marker. The difference between the first coordinate system and the second coordinate system may include a first difference indicating a displacement of the origin of the second coordinate system relative to the origin of the first coordinate system. The first difference may indicate a displacement of the radiation isocenter of the medical system relative to the calibration point of the phantom. The difference between the first coordinate system and the second coordinate system may also include a second difference indicating one or more deflection angles of at least one axis of the second coordinate system relative to the corresponding axis of the first coordinate system. In some embodiments, the difference determination unit 630 may determine the difference based on the locations of the one or more markers in the one or more projection images and the coordinates of the one or more markers in the first coordinate system of the phantom. In some embodiments, the difference determination unit 630 may determine the difference based on the variation of shapes, sizes, or locations of the one or more markers in the one or more projection images.

In some embodiments, step 520 of the process 500 may be performed according to the process 600 for determining a difference between a first coordinate system and a second coordinate system illustrated in FIG. 6B. The process 600 may be executed by the medical system 100. For example, the process 600 may be implemented as a set of instructions (e.g., an application) stored in the storage 220. The processor 210 may execute the set of instructions, and when executing the instructions, the processor 210 may accordingly be directed to perform the process 600. The operations of the illustrated process presented below are intended to be illustrative. In some embodiments, the process may be accomplished with one or more additional operations not described, and/or without one or more of the operations discussed. Additionally, the order in which the operations of the process as illustrated in FIG. 6B and described below is not intended to be limiting.

In 615, the difference determination module 420 (e.g., the image obtaining unit 610) may obtain one or more projection images of a phantom with at least one marker. In some embodiments, the image obtaining unit 610 may obtain the one or more projection images of the phantom from the image obtaining module 410 and/or the storage 220. The one or more projection images may include a plurality of projection data of the phantom, a plurality of projection data of the at least one marker of the phantom, etc. In some embodiments, the plurality of projection data may be obtained by scanning the phantom using the medical system at one or more gantry angles. The one or more gantry angles may include values from 0° to 360°. For example, the gantry angle may include 10°, 20°, 30°, 50°, etc.

In some embodiments, the phantom may have a cylindrical, cubic, spherical shape, or be a phantom in a shape of scaffold. The phantom may include one or more markers (e.g., ball bearings, rods, rings) on the surface of or embedded in the phantom. The markers may not be in the same plane. For example, the phantom may be a cylindrical phantom (or a cubic phantom) with multiple ball bearings embedded in the cylindrical phantom (or the cubic phantom) in a skewed helical trajectory. The number of the ball bearings may not be less than eight. For example, the number of the ball bearings may be 8, 9, 13, 17, etc. As another example, the phantom may be a cylindrical phantom with a rod in the center axis of the cylindrical phantom, a ring encased in the cylindrical phantom and the plane of the ring perpendicular to the center axis of the cylindrical phantom, and two ball bearings embedded in the cylindrical phantom symmetrical with respect to the ring and a line connecting the two ball bearings parallel to the center axis of the cylindrical phantom (e.g., the cylindrical phantom 710 in FIGS. 7A and 7C).

In some embodiments, the attenuation coefficient of the one or more markers on the phantom may be different from that of the phantom. For example, the attenuation coefficient of the one or more markers may be larger or less than that of the phantom. Besides, the attenuation coefficient of the one or more markers on the phantom may be the same or different. Thus, the projection image of the phantom may include information of the one or more markers, and the information of the one or more markers may be identified in the projection image of the phantom by the difference determination module 420. As shown in FIGS. 7A and 7C, the body of the phantom 710 may provide mechanical support to the marker(s) 720 (or 730, or 740). A marker 720 (or 730, or 740) may be embedded or enclosed in the body of the phantom 710. Compared to the marker 720 (or 730, or 740), the body of the phantom 710 may have none, negligible, or reduced signal in response to the X-rays emitted by the source of the scanner being analyzed, and thus the marker 720 (or 730, or 740) may be distinguished from the body of the phantom 710 in a CT image of the phantom 710. In some embodiments, the body of the phantom 710 may be made of a low density material, such as, delrin, polystyrene, etc. The marker 720 (or 730, or 740) may be made of a high density material, such as, tungsten, steel, etc.

In 625, the difference determination module 420 (e.g., the feature determination unit 620) may determine at least one feature of the at least one marker in the one or more projection image. The at least one feature of the at least one marker may include a shape of the at least one marker, a size of the at least one marker, or a location of the at least one marker in the one or more projection images. In some embodiments, the feature may include relative locations between any two of the one or more markers in the one or more projection images.

In 635, the difference determination module 420 (e.g., the difference determination unit 630) may determine the difference between the first coordinate system and the second coordinate system based on the at least one feature of the at least one marker. The difference between the first coordinate system and the second coordinate system may include a first difference indicating a displacement of the origin of the second coordinate system relative to the origin of the first coordinate system. In some embodiments, the first difference may be represented by a vector including three elements. The first element of the vector representing the first difference may be a position deviation of the origin of the second coordinate system relative to the origin of the first coordinate system in the x-axis of the first coordinate system. The second element of the vector representing the first difference may be a position deviation of the origin of the second coordinate system relative to the origin of the first coordinate system in the y-axis of the first coordinate system. The third element of the vector representing the first difference may be a position deviation of the origin of the second coordinate system relative to the origin of the first coordinate system in the z-axis of the first coordinate system. The value of any of the three elements of the vector representing the first difference may be a suitable value. In some embodiments, one of the three elements of the vector representing the first difference may be zero. The difference between the first coordinate system and the second coordinate system may also include a second difference indicating one or more deflection angles of at least one axis of the second coordinate system relative to the corresponding axis of the first coordinate system. For example, the second difference may include a deflection angle of the $x_f$-axis of the second coordinate system relative to the x-axis of the first coordinate system, a deflection angle of the $y_f$-axis of the second coordinate system relative to the y-axis of the first coordinate system, a deflection angle of the $z_f$-axis of the second coordinate system relative to the z-axis of the first coordinate system, or any combination thereof.

FIGS. 7A and 7C illustrate exemplary scenarios in which a phantom (e.g., the cylindrical phantom 710) is in different states. As shown in FIG. 7A, the first coordinate system of the phantom overlaps with the second coordinate system of the medical system. Specifically, the calibration point of the phantom overlaps with the radiation isocenter of the medical system (i.e., the first difference is zero). As shown in FIG. 7C, relative to the state where the phantom 710 is in FIG. 7A, the phantom is in a different state. The difference between the first coordinate system and the second coordinate system may be represented in connection with FIGS. 7E and 7F. The first difference may be represented by a vector T(t1, t2, t3) shown in FIG. 7E. t1 represents a position deviation of the origin $o_f$ of the second coordinate system (i.e., the radiation isocenter of the medical system) relative to the origin o of the first coordinate system (i.e., the calibration point) in the x-axis of the first coordinate system. t2 represents a position deviation of the origin $o_f$ of the second coordinate system (i.e., the radiation isocenter of the medical system) relative to the origin o of the first coordinate system (i.e., the calibration point) in the y-axis of the first coordinate system. t3 represents a position deviation of the origin $o_f$ of the second coordinate system (i.e., the radiation isocenter of the medical system) relative to the origin o of the second coordinate system (i.e., the calibration point) in the z-axis of the first coordinate system.

FIG. 7F shows an exemplary second difference between the first coordinate system and the second coordinate system. As shown in FIG. 7F, angle α represents a deflection angle of the $y_f$-axis of the second coordinate system relative to the y-axis of the first coordinate system. Angle β represents a deflection angle of the $x_f$-axis of the second coordinate system relative to the x-axis of the first coordinate system. Angle γ represents a deflection angle of the $z_f$-axis of the second coordinate system relative to the z-axis of the first coordinate system. Any one of the three deflection angles may be determined based on the other two deflection angles. For example, the angle γ can be determined according to the deflection angle α and the deflection angle β.

In some embodiments, the difference determination unit 630 may determine the difference between the first coordinate system and the second coordinate system using a geometric calibration method.

An exemplary phantom with markers is shown in FIGS. 7A and 7C. The phantom (the cylindrical phantom 710) includes two ball bearings 720 with the same size, one rod 730, and one ring 740. The rod 730 is in the axis of the cylindrical phantom 710 (i.e., the y-axis). The center of the rod 730 overlaps with the center axis of the cylindrical phantom 710. The ring 740 wings the cylindrical phantom 710. The rod 730 may be perpendicular to a plane where the ring 740 is. In some embodiments, the ring 740 may be a full circle. Alternatively, the ring 740 may be a portion of a full circle. A line connecting the two ball bearings 720 is parallel to the center axis of the cylindrical phantom 710 (i.e., the y-axis of the first coordinate system). The two ball bearings 720 are symmetric relative to the ring 740.

For the purpose of illustration, FIGS. 7B and 7D show projection images of a phantom (e.g., the cylindrical phantom 710) that is scanned at one gantry angle (e.g., 0°). If the first difference and the second difference is 0 (i.e., the first coordinate system overlaps with the second coordinate system), the features of the markers in the projection image may be shown in FIG. 7B. As shown in FIG. 7B, the two ball bearings 720 in the projection image are still symmetric points 721 with the same size, the rod 730 in the projection image is a line 731 parallel to the $y_f$-axis shown in FIG. 7A and the ring 740 in the projection image is a line 741 perpendicular to the line 731.

FIG. 7D shows an exemplary projection image including features of the markers corresponding to the scenario in FIG. 7C. As shown in FIG. 7D, the two ball bearings 720 in the projection image are two asymmetric points 721' with different sizes. The rod 730 in the projection image is a line 731' with a deflection angle relative to the $y_f$-axis shown in FIG. 7C. The ring 740 in the projection image is an ellipse 741' (or a portion of an ellipse). Besides, the relative locations of the two ball bearings 720, the rod 730, and the ring 740 in the projection image are changed with respect to those in FIG. 7B. It should be understood that the conditions in FIGS. 7B and 7D are illustrative and are not intended to be limiting. In some embodiments, the difference determination module 420 may determine the difference between the first coordinate system and the second coordinate system using other geometric calibration method. For example, for a cylindrical phantom with a plurality of ball bearings (e.g., eight ball bearings), the difference determination module 420 may determine the difference between the first coordinate system and the second coordinate system based on the locations of the plurality of ball bearings in the projection images at different gantry angles. In some embodiments, for a cylindrical phantom with one or more markers (e.g., eight ball bearings), the difference determination module 420 may determine locations of the one or more markers in the projection images at different gantry angles. The difference determination module 420 may obtain the coordinates of the one or more markers in the first coordinate system of the phantom. The difference determination module 420 may determine a relationship between the locations of the one or more markers in the projection images and coordinates of the one or more markers in the first coordinate system. The difference determination module 420 may determine the difference based on the relationship between the locations of the one or more markers in the projection images and the coordinates of the one or more markers in the first coordinate system. It should be noted that the above description about the determination of the difference between the first coordinate system and the second coordinate system is merely an example, and is not intended to be limiting. In some embodiments, other geometric calibration technique may also be used to determine the difference between the first coordinate system and the second coordinate system. All these are within the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, system, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:

1. A system, comprising:
   at least one storage device storing a set of instructions;
   at least one processor in communication with the at least one storage device, wherein when executing the set of instructions, the at least one processor is configured to cause the system to:
   determine a difference between a first coordinate system related to a phantom and a second coordinate system of a medical device of the system, wherein the difference between the first coordinate system and the second coordinate system includes a difference indicating one or more deflection angles of at least one axis of the second coordinate system relative to at least one corresponding axis of the first coordinate system;
   adjust the phantom to an updated state according to the difference between the first coordinate system and the second coordinate system such that the first coordinate system overlaps with the second coordinate system; and
   adjust an alignment device according to the phantom in the updated state to make laser beams emitted by the alignment device intersect at a radiation isocenter of radiation beams emitted by a radiation source of the medical device.

2. The system of claim 1, wherein an origin of the first coordinate system overlaps with a calibration point of the phantom.

3. The system of claim 2, wherein the calibration point of the phantom comprises a center of the phantom or a point of the phantom away from the center of the phantom by a distance.

4. The system of claim 1, wherein
the phantom includes at least one marker, and
to determine the difference between the first coordinate system and the second coordinate system, the at least one processor is further configured to cause the system to:
obtain one or more projection images of the phantom;
determine at least one feature of the at least one marker in the one or more projection images, the feature including at least one of: a shape of the at least one marker, a size of the at least one marker, or a location of the at least one marker in the one or more projection images; and
determine the difference between the first coordinate system and the second coordinate system based on the at least one feature of the at least one marker.

5. The system of claim 1, wherein the difference between the first coordinate system and the second coordinate system further includes:
a difference indicating a displacement of an origin of the second coordinate system relative to an origin of the first coordinate system.

6. The system of claim 1, wherein the system instructs a movable support to adjust the phantom.

7. The system of claim 6, wherein the movable support is an at least 4D movable support.

8. The system of claim 1, wherein the laser beam emitted by the alignment device has two planes perpendicular to each other.

9. The system of claim 1, wherein the laser beam emitted by the alignment device includes one plane.

10. The system of claim 1, wherein
the phantom includes one or more surface indicators; and
the laser beams emitted by the alignment device align with the one or more surface indicators of the phantom after the alignment device is adjusted.

11. The system of claim 10, wherein each of the one or more surface indicators includes a cross.

12. A method implemented on one system, including at least one processor and at least one storage, the method comprising:
determining a difference between a first coordinate system related to a phantom and a second coordinate system of a medical device of the system, wherein the difference between the first coordinate system and the second coordinate system includes a difference indicating one or more deflection angles of at least one axis of the second coordinate system relative to at least one corresponding axis of the first coordinate system;
adjusting the phantom to an updated state according to the difference between the first coordinate system and the second coordinate system such that the first coordinate system overlaps with the second coordinate system; and
adjusting an alignment device according to the phantom in the updated state to make laser beams emitted by the alignment device intersect at a radiation isocenter of radiation beams emitted by a radiation source of the medical device.

13. The method of claim 12, wherein an origin of the first coordinate system overlaps with a calibration point of the phantom.

14. The method of claim 13, wherein the calibration point of the phantom comprises a center of the phantom or a point of the phantom away from the center of the phantom by a distance.

15. The method of claim 12, wherein
the phantom includes at least one marker, and
the determining the difference between the first coordinate system and the second coordinate system further comprising:
obtaining one or more projection images of the phantom;
determining at least one feature of the at least one marker in the one or more projection images, the feature including at least one of: a shape of the at least one marker, a size of the at least one marker, or a location of the at least one marker in the one or more projection images; and
determining the difference between the first coordinate system and the second coordinate system based on the at least one feature of the at least one marker.

16. The method of claim 12, wherein the difference between the first coordinate system and the second coordinate system further includes:
a difference indicating a displacement of an origin of the second coordinate system relative to an origin of the first coordinate system.

17. The method of claim 12, wherein the phantom is adjusted by a movable support.

18. The method of claim 17, wherein the movable support is an at least 4D movable support.

19. The method of claim 12, wherein the laser beam emitted by the alignment device has two planes perpendicular to each other.

20. A non-transitory computer readable medium comprising executable instructions that, wherein when executed by at least one processor, the executable instructions cause the at least one processor to effectuate a method comprising:
determining a difference between a first coordinate system related to a phantom and a second coordinate system of a medical device of a system, wherein the difference between the first coordinate system and the second coordinate system includes a difference indicating one or more deflection angles of at least one axis of the second coordinate system relative to at least one corresponding axis of the first coordinate system;
adjusting the phantom to an updated state according to the difference between the first coordinate system and the second coordinate system such that the first coordinate system overlaps with the second coordinate system; and
adjusting an alignment device according to the phantom in the updated state to make laser beams emitted by the aligment device intersect at a radiation isocenter of radiation beams emitted by a radiation source of the medical device.

* * * * *